United States Patent [19]

Betts et al.

[11] Patent Number: 5,046,496

[45] Date of Patent: Sep. 10, 1991

[54] SENSOR ASSEMBLY FOR MEASURING ANALYTES IN FLUIDS

[75] Inventors: Ronald E. Betts, LaJolla; David W. Deetz, Del Mar, both of Calif.

[73] Assignee: PPG Industries, Inc., Pittsburgh, Pa.

[21] Appl. No.: 343,234

[22] Filed: Apr. 26, 1989

[51] Int. Cl.$^5$ ............................................. A61B 5/00
[52] U.S. Cl. .................................. 128/635; 204/403; 204/409
[58] Field of Search ............... 128/635, 763, 767, 653; 204/403, 409; 525/524

[56] References Cited

U.S. PATENT DOCUMENTS

| | | | |
|---|---|---|---|
| 2,637,316 | 5/1953 | Grez | 128/2.1 |
| 3,000,805 | 9/1961 | Carritt et al. | 128/635 X |
| 3,049,118 | 8/1962 | Arthur et al. | 128/635 |
| 3,399,162 | 8/1968 | Salame | 525/524 X |
| 3,497,442 | 2/1970 | Vincent | 128/635 X |
| 3,674,012 | 7/1972 | Sage | 128/2.1 R |
| 3,732,079 | 5/1973 | Davis | 23/253 TP |
| 3,734,079 | 5/1973 | Weber | 128/2 G |
| 3,844,275 | 10/1974 | Elliott | 128/2.1 E |
| 4,083,363 | 4/1978 | Philpot, Jr. | 128/2 G |
| 4,312,332 | 1/1982 | Zick | 128/635 |
| 4,339,317 | 7/1982 | Meiattini et al. | 204/195 B |
| 4,385,637 | 5/1983 | Akhari | 128/767 X |
| 4,553,552 | 11/1985 | Valdespino et al. | 128/637 |
| 4,608,996 | 9/1986 | Brown | 128/760 |
| 4,615,340 | 10/1986 | Cronenberg et al. | 128/635 |
| 4,703,762 | 11/1987 | Rathbone et al. | 128/763 |
| 4,734,184 | 3/1988 | Burleigh et al. | 204/409 |
| 4,899,759 | 2/1990 | Pederson et al. | 128/693 |

FOREIGN PATENT DOCUMENTS

| | | |
|---|---|---|
| 376117 | 10/1984 | Austria . |
| 0306158 | 3/1989 | European Pat. Off. . |
| 0317847 | 5/1989 | European Pat. Off. . |
| 0327039 | 8/1989 | European Pat. Off. . |
| 0351516 | 1/1990 | European Pat. Off. . |
| 1036539 | 8/1958 | Fed. Rep. of Germany ...... 204/403 |
| 1038310 | 9/1958 | Fed. Rep. of Germany ...... 204/403 |

Primary Examiner—Lee S. Cohen
Attorney, Agent, or Firm—Kenneth J. Stachel

[57] ABSTRACT

A sensor assembly for measuring analytes in fluids, e.g., blood, is described. The sensor assembly comprises a housing in the form of a flow-through cell containing one or more microsensors the housing disposed on the distal end of a hypodermic syringe.

14 Claims, 1 Drawing Sheet

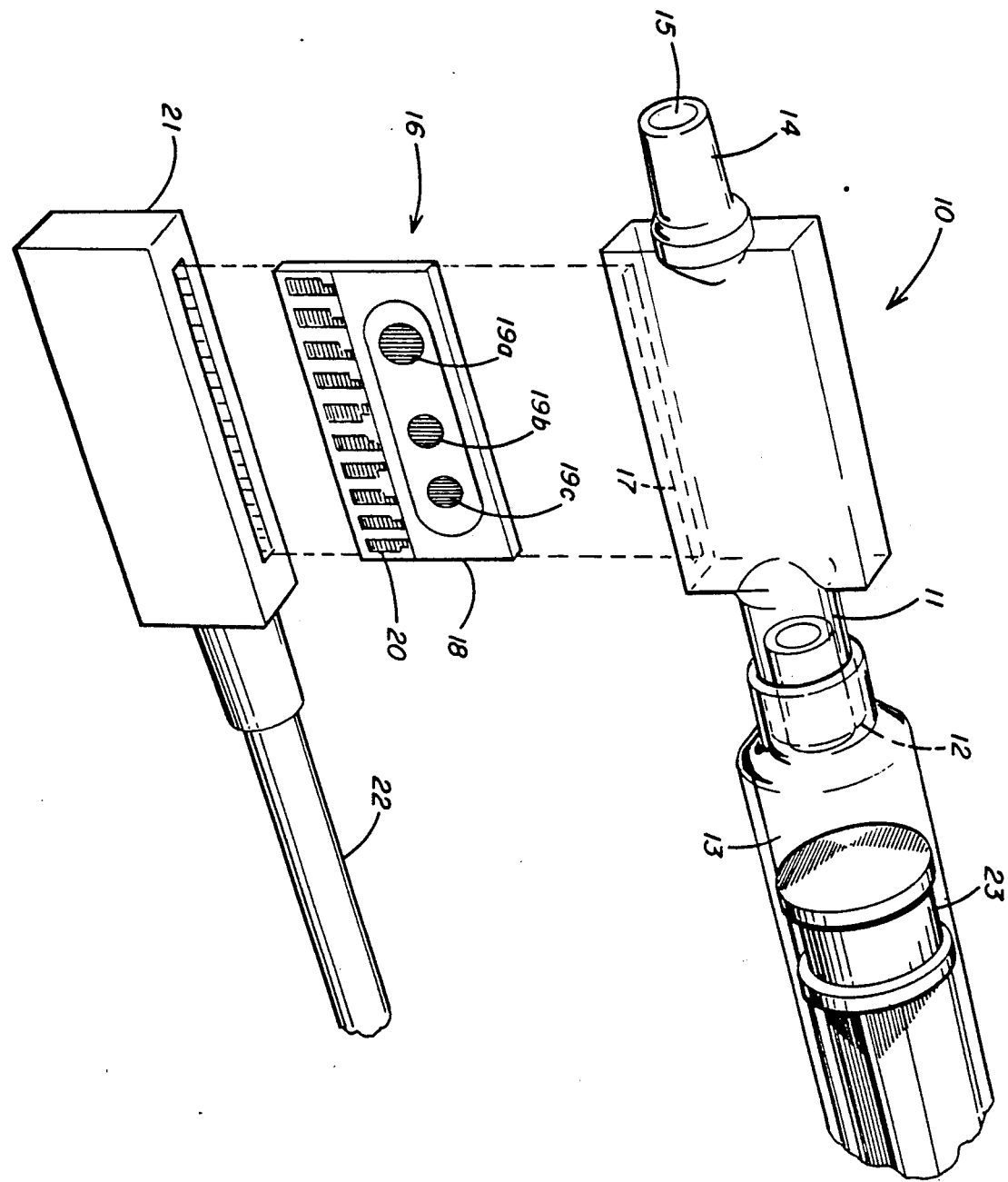

SENSOR ASSEMBLY FOR MEASURING ANALYTES IN FLUIDS

BACKGROUND OF THE INVENTION

Portable devices embodying miniature electrodes or microsensors for measuring analytes, e.g., pH, $pO_2$, $PCO_2$, in fluids such as blood are known and described, e.g., in U.S. Pat. No. 4,339,317 and U.S. Pat. No. 4,615,340. The '340 patent describes a hand-held sensor assembly comprising a reusable housing portion having sensor electrode means contained therein and a detachable, disposable blood sampler portion associated therewith. The '317 patent describes a disposable hypodermic syringe, the reusable piston of which has a plurality of microelectrodes disposed in its face.

The present invention provides a sensor assembly that is convenient to use and offers the advantage of being completely disposable after a single use. Also, since the sensor electrodes are calibrated immediately before use, accurate, error-free measurements are assured.

DESCRIPTION OF THE DRAWING

The appended drawing is an exploded perspective view of a sensor assembly for measuring analytes in fluids, e.g. blood, in accordance with this invention.

DESCRIPTION OF THE INVENTION

With reference to the drawing the sensor assembly of the invention comprises a housing 10 having a generally planar box-like configuration which functions as a flow-through cell. The housing 10 has a proximate end 11 with an inlet port 12 formed therein the proximate end 11 of the housing 12 being adapted for engagement by, e.g., a LUER-LOK connection, with the distal end 13 of a conventional hypodermic syringe. The distal end 14 of housing 10 having outlet port 15 formed therein is adapted for engagement with means (not shown) for withdrawing blood sample from a subject, e.g. a hypodermic needle or an arterial catheter.

An electrode assembly 16 is inserted into housing 10 through slot 17 and secured therein by a suitable adhesive. The electrode assembly 16 comprises a rectangular ceramic substrate 18 having formed thereon one or more conventional miniaturized electrodes or microsensors. In a preferred embodiment three such microsensors 19a, 19b and 19c would be employed capable of sensing pH, $pCO_2$ and $pO_2$ respectively.

The microsensors 19 are fabricated in known fashion by, e.g., a thick film processing technique. The pH sensor 19a may be, e.g., be a PVC membrane type ion selective electrode. Contained within the PVC membrane is an ionophore selective to the $H^+$ion, typically, tridodecylamine. Although other pH sensors can be used, since the pH sensor is in direct contact with the blood the type described is preferred.

The $pCO_2$ sensor 19b may be of a modified Stow-Severinghouse type which employs a pH sensor to measure the pH change of an electrolyte, the electrolyte being isolated from the blood by a $CO_2$ permeable, $H^+$ion permeable membrane The pH of the electrolyte is proportional to $CO_2$ partial pressure.

The $pO_2$ sensor 19c may be a polarographic Clark cell having an anode, cathode, supporting electrolyte and oxygen permeable membrane. The sensor outputs an electrical current directly proportional to $O_2$ partial pressure.

Since operation of the sensing mechanism is temperature dependent, it is necessary to either control the sensor temperature via a heater and thermostat or compensate for temperature changes. Thus, a heater and temperature sensing thermistor are integrated into the ceramic substrate along with the sensors. The heater and thermistor are also fabricated, in known fashion, by a thick film processing technique.

The electrode assembly 16 is provided with a bank of edge connectors 20 which plug into a mating female connector 21 connected by electrical cable 22 to a suitable hand-held, preferably battery powered, monitoring instrument or analyzer (not shown). Of course, other suitable means of linking the sensor assembly to the monitoring instrument may be used.

The monitoring instrument is also conventional, employing state of the art technology to receive and process signals from the sensors and display information to the operator regarding the value of the blood analytes being measured, e.g., pH, $pCO_2$, $pO_2$.

In use, it is contemplated that housing 10 containing electrode assembly 16 would be prefabricated as a unit and packaged along with a conventional hypodermic syringe and a conventional sterile, disposable hypodermicsneedle. Since both the housing/electrode assembly unit as well as the syringe are intended to be used only once and disposed of, the housing and syringe are preferably made of a suitable inexpensive plastic, e.g., polyethylene, polypropylene, polyvinylidene chloride or the like.

In operation the proximate end 11 of the housing/electrode assembly unit is connected to the distal end 13 of the syringe and the distal end 14 is connected to the hub of the hypodermic needle (or the proximate end of an arterial catheter). Electrical connections are then made between the electrode assembly and the monitoring instrument and the microsensors are calibrated by contacting the microsensors with a standard calibration solution. The calibration solution is then expelled by operation of syringe piston 23 and a blood sample is drawn into the syringe through the housing/electrode assembly unit and the desired analytes are measured. The sensor assembly is then disconnected from the monitoring instrument and discarded.

Regarding calibration, the same involves contacting the microsensors with a solution of known pH, $pCO_2$ and $pO_2$ levels, measuring the microsensor outputs and calculating calibration coefficients to use in software algorithims, all of which is conventional and known to the art. See, e.g., U.S. Pat. No. 4,734,184.

Producing a calibration solution of known $pO_2$, $pCO_2$ and pH values is straight forward; however, maintaining those values in a small, disposable, inexpensive and easy to use container is not. The container must not be "transparent" to $O_2$ and $CO_2$, i.e., it must not allow an exchange of $O_2$ and $CO_2$ with the environment. The conventional container for calibration solution is a glass "snap-top" ampule, which though small and disposable is not inexpensive and easy to use. It would be desirable to use inexpensive Plastics, such as polyethylene, polypropylene, polyvinylidene chloride or the like to fabricate disposable containers or ampules to store calibration solution until use, without any significant exchange of $O_2$ and $CO_2$ values with the environment. However, since such inexpensive plastics are permeable to $O_2$ and $CO_2$, the same must be provided with a suitable barrier coating which substantially reduces $O_2$ and $CO_2$ permeability. Such coatings are essentially gas impermeable organic thermoset resins.

Suitable barrier coatings are described in copending, commonly assigned U.S. Pat. application Ser. No. 152,176 filed Feb. 4, 1988, now abandoned the teachings of which respecting the composition and preparation of such coatings are incorporated by reference herein. Generally speaking, the barrier coatings disclosed in U.S.S.N. 152,176 comprise ungelled amine-functional polymeric resin reaction product of a polyamine having up to two primary amino nitrogen groups per molecule and a polyepoxide. A particularly preferred barrier coating comprises the reaction product of an adduct of tetraethylenepentamine and 1-methoxy-2-propanol with a diglycidyl ether of bisphenol A.

Rather than provide a separate container for the calibration solution, in an embodiment of this invention, the calibration solution would be contained within the syringe portion of the sensor assembly, in which case the syringe would be coated with the aforementioned barrier coating. In this embodiment, the housing/electrode assembly unit would be packaged along with a coated syringe containing the calibrant solution, calibrant solution being passed from the syringe through the housing/electrode assembly unit immediately prior to taking the blood sample.

A principle feature of the assembly according to the invention is that the housing/electrode assembly unit or measuring chamber is "flow-thru", thus eliminating the need to purge the arterial catheter or the measuring chamber of non-blood constitutents prior to use. A non-flow-thru design requires purging of non-blood constitutents, otherwise a mixed sample would result with attendant inaccurate results.

Although the invention has been described in some detail by the foregoing, it is to be understood that many variations may be made therein without departing from the spirit and scope thereof as defined by the appended claims.

We claim:

1. Sensor assembly for measuring analytes in fluids comprising:

a syringe having a body portion with a piston slidable therein, said syringe having a distal end with an outlet port formed therein;

a housing that is a flow through cell having a proximate end with a port formed therein and a distal end with another port formed therein, where the proximate end of the housing engages with and connects to the distal end of the syringe so that a sample of fluid can be drawn through the housing by the syringe, the distal end of the housing adapted for engagement with means for withdrawing a sample of fluid;

sensing means disposed within said housing as an electrode assembly having at least one microsensor prepared by thick film processing for sensing at least one analyte in the sample of fluid including means for connecting said sensing means into a circuit and transmitting a signal to monitor means which measures and displays the value of the analyte sensed by the sensing means.

2. The sensor assembly of claim 1 wherein the fluid is blood and the distal end of the housing has a means for engagement through the other part with the means for withdrawing blood sample that is a hypodermic needle or an arterial catheter.

3. The sensor assembly of claim 1 wherein the sensing means has an electrode assembly that enables sensing of pH, $PCO_2$, and $pO_2$.

4. The sensor assembly of claim 1, wherein the electrode assembly of the sensing means is comprised of a ceramic substrate disposed within an coplanar with said housing, the substrate having formed thereon at least one thick film microsensor means for sensing at least one blood analyte.

5. The sensor assembly of claim 4 wherein the substrate has formed thereon three microsensor means for respectively sensing pH, $pCO_2$, and $pO_2$.

6. The sensor assembly of claim 5, wherein the electrode assembly of the sensing means has electric connectors and the sensing means includes a mating connector for the electric connectors of the electrode assembly and includes a cable connected to the mating connector.

7. The sensor assembly of claim 4, wherein the sensing means includes a heater and temperature sensing thermistor integrated onto the ceramic substrate with the at least one thick film microsensor means.

8. The sensor assembly of claim 1 wherein the syringe and associated piston and the housing are formed of plastic material.

9. The sensor assembly of claim 8 wherein the plastic material is polypropylene.

10. The sensor assembly of claim 1 wherein the sensing means are in direct contact with the fluid that is measured for analytes.

11. The sensor assembly of claim 1 wherein the sensing means includes a heater.

12. The sensor assembly of claim 1 wherein the sensing means includes a temperature sensing thermistor.

13. The sensor assembly of claim 1 that includes a means for withdrawing connected to the distal end of the housing and wherein the means for withdrawing and the distal and proximate ends of the housing and the distal end of the syringe are in alignment.

14. The sensor assembly of claim 1 wherein the electrode assembly is a ceramic substrate with a plurality of thick film microsensors.

* * * * *

UNITED STATES PATENT AND TRADEMARK OFFICE
CERTIFICATE OF CORRECTION

PATENT NO. : 5,046,496
DATED : September 10, 1991
INVENTOR(S) : Betts, et al.

It is certified that error appears in the above-indentified patent and that said Letters Patent is hereby corrected as shown below:

At column 4, Claim 2, line 11, "part" should be --port--.

At column 4, Claim 3, line 16, "PCO$_2$" should be --pCO$_2$--.

At column 4, Claim 4, line 19, "an" should be --and--.

Signed and Sealed this

Twenty-third Day of August, 1994

Attest:

BRUCE LEHMAN

*Attesting Officer*  *Commissioner of Patents and Trademarks*